United States Patent [19]
Taschner

[11] Patent Number: 5,725,830
[45] Date of Patent: Mar. 10, 1998

[54] SEAL FOR A STERILIZING CONTAINER

[75] Inventor: Wolfgang Taschner, Tuttlingen, Germany

[73] Assignee: Aesculap AG, Tuttlingen, Germany

[21] Appl. No.: 188,430

[22] Filed: Jan. 28, 1994

Related U.S. Application Data

[63] Continuation of Ser. No. 838,427, Mar. 5, 1992, Pat. No. 5,328,661.

[30] Foreign Application Priority Data

Jul. 19, 1990 [DE] Germany .......................... 40 22 952.1

[51] Int. Cl.[6] .................................................. A61L 2/00
[52] U.S. Cl. ...................... 422/56; 422/300; 422/310; 422/119; 206/459.1; 206/807; 116/200
[58] Field of Search .......................... 422/26, 56, 300, 422/302, 295, 297, 310; 206/459.1, 807; 220/214; 215/250; 116/200; 292/307 A

[56] References Cited

U.S. PATENT DOCUMENTS

| | | | |
|---|---|---|---|
| 1,602,309 | 10/1926 | Martineau | 292/307 A |
| 3,034,819 | 5/1962 | Tupper | 206/807 |
| 3,484,036 | 12/1969 | Meyers | 206/807 |
| 3,924,800 | 12/1975 | Desmond et al. | 206/807 |
| 3,972,416 | 8/1976 | Underwood | 206/459.1 |
| 4,509,196 | 4/1985 | Sak et al. | 206/807 |
| 4,625,885 | 12/1986 | Nichols | 220/214 |
| 4,682,688 | 7/1987 | Budert | 206/807 |
| 4,783,321 | 11/1988 | Spence | 422/300 |
| 5,225,162 | 7/1993 | Stoirille | 422/56 |
| 5,328,661 | 7/1994 | Taschner | 422/56 |

*Primary Examiner*—Hien Tran
*Attorney, Agent, or Firm*—Barry R. Lipsitz

[57] ABSTRACT

A sterilizing container is provided with a seal. The container has a lower part, a cover sealingly placeable thereon, and a closure for securing the cover on the lower part. A seal secures the closure in the closed position. The seal is formed in a planar substrate, such as paper or paperboard, and includes a bar or finger insert element that is insertable into a loop that projects from the closure of the container. The seal is provided with a region adjacent to the free end of the insert element that is coated with contact adhesive. This region is foldable along a fold line to form an unreleasable seal with the free end of the insert element.

9 Claims, 1 Drawing Sheet

SEAL FOR A STERILIZING CONTAINER

This application is a continuation of application Ser. No. 07/838,427, filed Mar. 5, 1992, now U.S. Pat. No. 5,328,661.

The invention relates to a seal for a sterilizing container for receiving surgical instruments or the like, comprising a lower part, a cover sealingly placeable thereon, a closure means securing the cover on the lower part as well as a seal for securing the closure means in the closed position, wherein the seal comprises a bar-like or finger-like insert element insertable into a loop of the closure means and a connector connected to the rear end of the insert element not inserted into the loop and unreleasably connectable with the end of the insert element protruding through the loop.

In the case of sterilizing containers care must be taken that the container is not opened unintentionally following sterilizing so that the sterility of the contents is ensured. In order to achieve this, it is known to seal the closure means of such sterilizing containers, using, for example, wire seals or plastic seals in the manner of cable binders. The known seals are attached by the insert element being locked in position on a connector by deformation, form-locking or a detent connection after its insertion into a loop of the closure means. This connection can no longer be released, i.e. this is possible only by breaking the seal.

The closure means of the sterilizing container cannot be opened as long as the seal is attached so that any opening of the closure means presupposes that the seal has been broken. This is easily recognizable from the closure means of a sterilizing container and so an undamaged seal is a sign that the container has not been opened unintentionally.

The object of the invention is to design a seal of the generic type such that it can be applied without any tools and without complicated provision of a form-locking or detent connection.

This object is accomplished in accordance with the invention, for a seal of the type described at the outset, in that the connector has a region coated with contact adhesive, this region being arranged adjacent to the free end of the insert element and foldable along a fold line onto the free end of the insert element. In order to close the seal it is sufficient to fold this coated region over and press it onto the free end of the insert element. This provides a firm adhesive connection which can be released again only when the seal is broken in particular, adhesives can be used for this which reach this strength only at the higher temperatures occurring during sterilizing. This means that prior to sterilization this closure means can, if necessary, be opened once more and closed again without breaking the seal. Only after sterilization is the connection so permanent that any opening can take place only once the seal is broken.

It is favourable for the region coated with contact adhesive to be covered with a removable cover film so that the region which can be folded over is made ready for closing the seal only when required by removing the cover film. A particularly favourable arrangement results when the fold line extends in front of the free end of the insert element at right angles to its longitudinal expansion. The shaft region which is folded over is therefore folded onto the forward part of the insert element and so the seal is altogether shorter due to this folding procedure.

In a preferred embodiment, the coated region is connected with the rear end of the insert element via two webs extending parallel to the insert element. This results in a symmetrical arrangement having high stability.

Preferably, the seal is plate-like or sheet-like in design, i.e. a larger number of seals can be stacked in piles in a magazine and removed therefrom as required.

Such a seal can be designed such that parallel slits are arranged in the seal on both sides of the insert element. The slits extend as far as the fold line and are connected with one another in the region of the fold line. These slits therefore form the insert element between them from the flat seal.

When the seal is notched at the end points of the fold line, folding over is made easier and, moreover, the operating personnel recognize the exact position of the fold line so that the danger of any folding at an undesired line is reduced.

It is favourable for the region coated with contact adhesive, in the folded over position, to also cover partial regions of the connector adjacent the free end of the insert element. This increases the mechanical stability of the seal which then has, for example, a symmetrical shape with two compact end regions and two intermediate, parallel slits which form between them the insert element which is fixed on both sides.

It is possible for the seal to consist of paperboard or paper or another material which is capable of being recycled. This facilitates the disposal of used seals.

BRIEF DESCRIPTION OF THE DRAWINGS

The following description of preferred embodiments of the invention serves to explain the invention in greater detail in conjunction with the drawings.

In the drawings.

Figure 1:
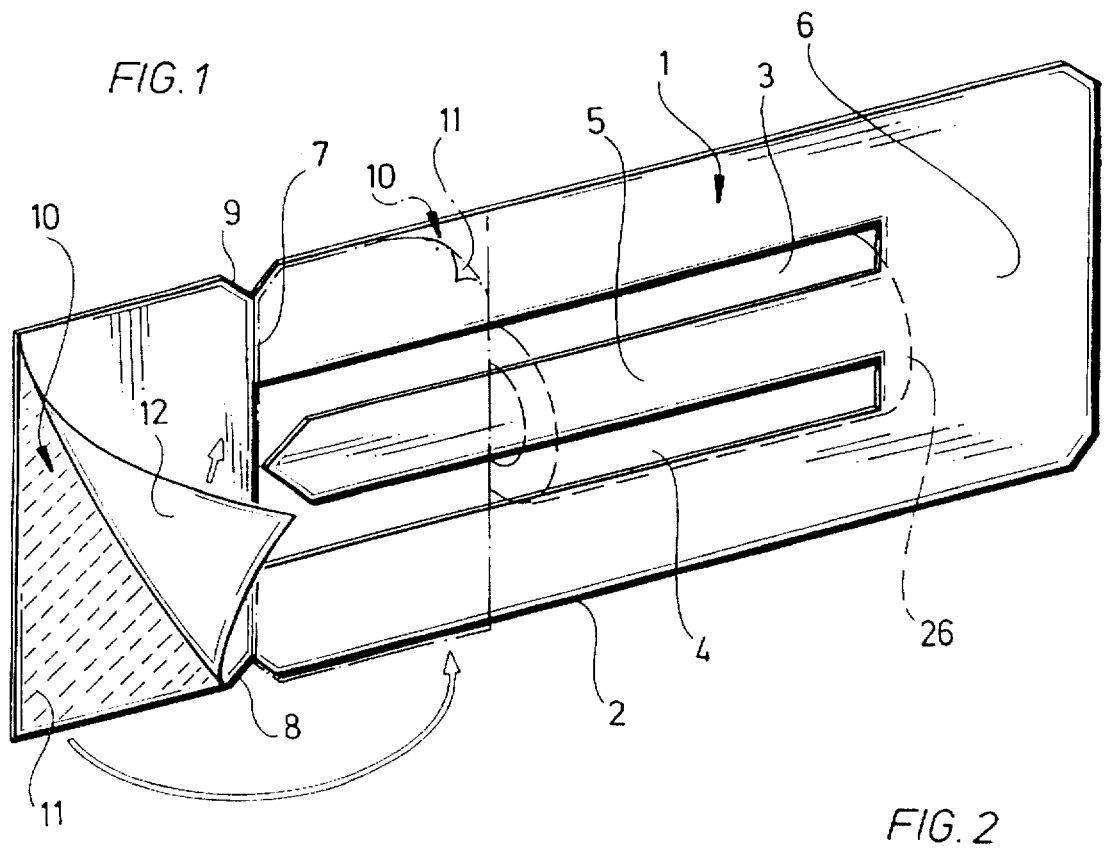
FIG. 1 is a perspective view of a seal prior to the region coated with contact adhesive being folded over and FIG. 2 is a view of a sterilizing container with an inserted and closed seal.

The seal 1 illustrated in FIG. 1 has the shape of a rectangular card or a rectangular sheet and consists of paper, paperboard or a similar material capable of being recycled. Two longitudinal slits 3 and 4 are spaced from one another and extend parallel to the longitudinal edges 2 of the seal 1. The slits are enclosed around one end by the material of the seal whereas, at the other end, they each expand towards the other longitudinal slit such that a connection is formed between the two longitudinal slits 3 and 4. Therefore, a tongue-like or finger-like insert element 5 is formed between the two longitudinal slits 3 and 4. At its rear end this insert element merges into the end region 6 of the seal 1 which has no slits whereas, at its front end, it ends in free space and is not connected to the surrounding material of the seal 1.

The two longitudinal slits 3 and 4 are limited at the free end of the insert element 5 by a fold line 7 extending transversely to the longitudinal direction of the longitudinal slits 3 and 4. The fold line extends as far as the longitudinal edges 2 of the seal and at its end points merges into notches 8 and 9 in the seal.

The region 10 following the fold line 7 is coated on one side with a contact adhesive 11 and this adhesive region is covered with a cover film 12 extending as far as the fold line 7.

Figure 2:
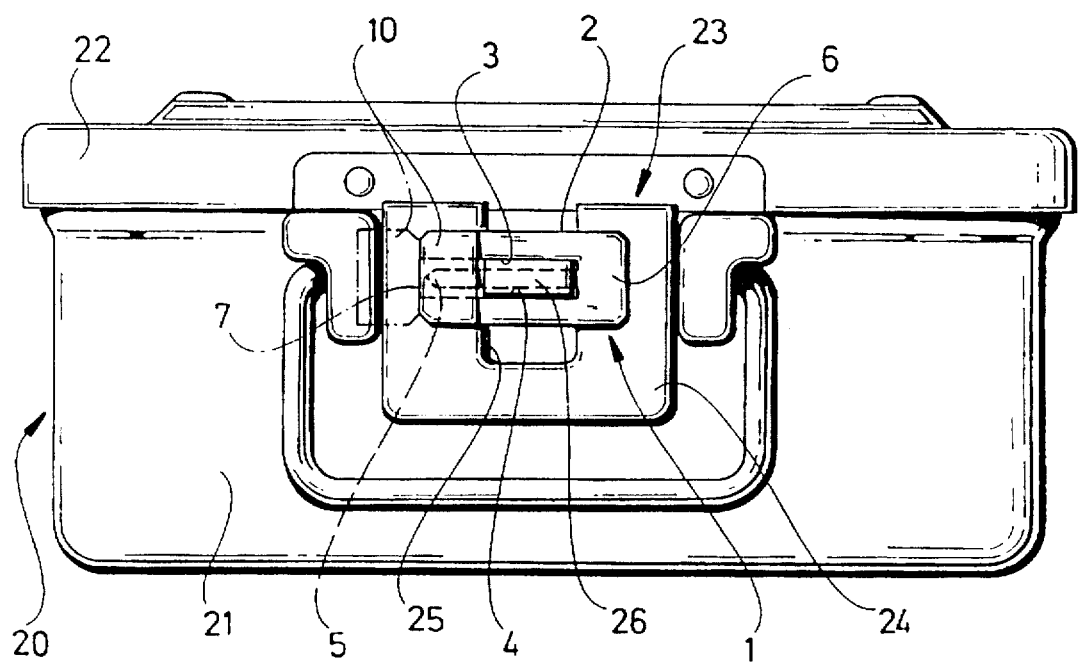

The seal as described can be used for sealing the closure means of a sterilizing container, as illustrated in FIG. 2. This sterilizing container 20 has a lower part 21 and a cover 22 which can be placed sealingly thereon. The cover 22 can be fixed in position on the lower part 21 by a closure means 23. The closure means comprises a flap 24 with a recess 25 through which, when the closure means is closed, a loop 26 arranged on the lower part 21 of the sterilizing container 20 protrudes. To open the closure means the flap 24 must be swivelled past the loop 26.

In order to seal this closure means in the closed position, the seal illustrated in FIG. 1 is used. When the flap 24 is closed, the insert element 5 is introduced with its free end into the loop 26 and pushed completely through this until the free end exits again on the opposite side of the loop. The end region 6 and the entire front part of the seal 1 hereby cover the flap 24.

Once the seal 1 has been inserted in this manner, the cover film 12 is removed from the region 10 coated with contact adhesive and this region is folded over along the fold line 7 and pressed down such that the contact adhesive engages adhesively on the free end of the insert element 5 and on the adjacent regions of the seal 1 simultaneously.

In FIG. 1, the seal is illustrated prior to the adhesive region 10 being folded over, the region 10 when folded over is illustrated by a dash-dot line.

In FIG. 2, the seal is illustrated on the container, the adhesive region 10 hereby being folded over onto the seal, i.e. the seal is secured in place. The dash-dot line represents the region 10 prior to being folded over.

I claim:

1. In combination:
   a sterilizing container having a lower part, a cover sealingly placeable on said lower part and closure means for securing said cover on said lower part, and
   a seal constructed and arranged to secure said closure means in a closed position, said seal comprising:
   an insert element extending from a connector member and having a free end insertable into a loop of said closure means; and
   a contact adhesive on a region of said connector member adjacent to said free end, said region being foldable along a fold line onto and into contact with said free end to enable said contact adhesive to form an unreleasable bond between said contact adhesive region and the free end of said insert element that is inserted into and extends beyond said loop.

2. A combination according to claim 1 further comprising a cover film on said contact adhesive region which is removable prior to effecting said unreleasable bond.

3. A combination according to claim 1 wherein said fold line extends perpendicularly to a longitudinal axis of said insert element and in front of said free end.

4. A combination according to claim 1 wherein said contact adhesive region is connected with a rear end of said insert element via two webs extending parallel to the insert element.

5. A combination according to claim 1 wherein said seal is fabricated as a planar article.

6. A combination according to claim 1 further comprising a notch at each end of said fold line.

7. A combination according to claim 1 wherein said region with contact adhesive thereon overlaps portions of said connector member in addition to said free end when the contact adhesive region is folded to form said unreleasable bond.

8. A combination according to claim 1 wherein said seal consists of paperboard or paper.

9. A combination according to claim 1 wherein said contact adhesive is responsive to temperature to form said unreleasable bond only after it has been exposed to sterilizing heat.

* * * * *